United States Patent [19]

Birtwistle et al.

[11] Patent Number: 5,139,781
[45] Date of Patent: Aug. 18, 1992

[54] TOPICAL COMPOSITION COMPRISING MONO- AND DI-ALKYL OR ALKENYL PHOSPHATES AND ALKYLAMIDOPROPYL BETAINES OF ALKYLAMPHOGLYCINATES

[75] Inventors: David H. Birtwistle, Wirral; Peter Carter, South Wirral, both of Great Britain

[73] Assignee: Chesebrough-Pond's USA Co., Division of Conopco, Inc., Greenwich, Conn.

[21] Appl. No.: 655,517

[22] Filed: Feb. 13, 1991

[30] Foreign Application Priority Data

Feb. 13, 1990 [GB] United Kingdom ............. 9003199

[51] Int. Cl.$^5$ ................ A61K 7/00; A61K 7/06
[52] U.S. Cl. ................ 424/401; 424/70; 424/57; 252/DIG. 5; 252/DIG. 13
[58] Field of Search ............. 424/70, 401, 57; 252/174.16, 546, DIG. 5, DIG. 7, DIG. 13, DIG. 17, DIG. 16

[56] References Cited

U.S. PATENT DOCUMENTS

| | | | |
|---|---|---|---|
| 2,758,093 | 8/1956 | Ernst et al. | 252/174.16 |
| 4,139,485 | 2/1979 | Imokawa et al. | 252/174.16 |
| 4,259,204 | 3/1981 | Hamma | 424/70 X |
| 4,375,421 | 3/1983 | Rubin et al. | 424/70 X |
| 4,526,710 | 7/1985 | Fujisawa et al. | 252/545 |
| 4,758,376 | 7/1988 | Hirota et al. | 252/174.16 |
| 5,015,471 | 5/1991 | Birtwistle et al. | 514/772 X |

FOREIGN PATENT DOCUMENTS 0179277  4/1986  European Pat. Off. .

Primary Examiner—Thurman K. Page
Assistant Examiner—Sally Gardner
Attorney, Agent, or Firm—Milton L. Honig

[57] ABSTRACT

A composition suitable for topical application to the skin or hair, comprises:
a. a monoalkyl or monoalkenyl phosphate surfactant,
b. a dialkyl or dialkenyl phosphate surfactant; and
c. a co-surfactant chosen from alkylamidopropyl betaines and alkylamphoglycinates.

19 Claims, No Drawings

TOPICAL COMPOSITION COMPRISING MONO- AND DI-ALKYL OR ALKENYL PHOSPHATES AND ALKYLAMIDOPROPYL BETAINES OF ALKYLAMPHOGLYCINATES

FIELD OF THE INVENTION

The invention relates to compositions suitable for topical application to the skin, (including the mucosae), and to the hair. In particular, the invention is concerned with highly improved detergent compositions suitable for cleansing the whole body surface, including the mouth.

BACKGROUND TO THE INVENTION & PRIOR ART

The damaging effect of conventional detergents used to wash the body surface, particularly where young, tender or damaged skin is involved, has been the subject of intense study for many years in a search for milder-to-the-skin products, which not only cleanse the skin efficiently, but also leave the skin with a pleasant smooth silky feel after the skin surface has been dried off.

The use of certain mono- and di-alkyl phosphate salts for this purpose has been advocated in view of their mild characteristics, but some of this group of salts are used as antifoam agents because of their lather suppressant properties, and would therefore require careful formulation if lather control is not required.

To this end, U.S. Pat. No. 4,139,485 (Kao Soap Co. Ltd.) describes a detergent composition having low irritation properties on human skin, wherein the surfactant component is dialkyl or dialkenyl phosphate salt (DAP) and/or monoalkyl or monoalkenyl phosphate salt (MAP), each alkyl or alkenyl group having from 10 to 16 carbon atoms), the Weight ratio of 'DAP' to 'MAP' being from 20:80 to 0:100. This system is stated to possess good detergency.

Also, U.S. Pat. No. 4,526,710 (Kao Corporation), report a study to improve properties of detergent composition which make use of anionic phosphate surface active agents, which Kao maintain are highly innocuous and particularly mild to the skin. As a result, Kao have found that when phosphate ester salts having a specific ion pair, notably mono- or di-alkyl (C8-18) phosphates, are used in combination with alkanol amine salts of higher fatty acids and alkyl amine oxides, the detergency and foaming characteristics are remarkably improved.

Also, U.S. Pat. No. 4,758,376 (Kao) discloses an alternative composition, comprising an alkanolamine salt of a mono or dialkyl (C8-18) phosphate or mixtures thereof, to that described in U.S. Pat. No. 4,526,710 in which the problem of poor foaming due to the dialkyl phosphate salt is dealt with by incorporating with the phosphate a compound chosen from an amidoamine amphoteric surfactant or hydroxysulphobetaine, or an aliphatic lactylate or glycolate.

While investigating Kao's teaching further, particularly their stipulation in U.S. Pat. No. 4,139,485 that the weight ratio of mono- to di-alkyl phosphate salt cannot fall below 80:20, without loss of foaming power, Applicants have now discovered that a greater proportion by weight of the dialkyl phosphate salt of Kao can be tolerated without significant loss of lather volume, provided there is also present a special co-surfactant. The compositions so obtained are accordingly capable of producing a superior lather volume and an outstanding lather creaminess. Also, the composition is so mild to the skin that it can safely be used for cleansing the mucosae, such as the mouth and the vagina, and other more delicate skin areas. It can also be used in shampoos for frequent, e.g. daily, hair washing, without risk of scalp irritation or damage attributable to harsher products. In addition to these excellent attributes, the ease of rinsing from hair or skin and superior silky-smooth after-use skin feel properties of the compositions, including freedom from skin roughness and erythema, have great consumer appeal.

DEFINITION OF THE INVENTION

Accordingly, the invention provides a composition suitable for topical application to the skin or hair, which comprises:

(a) from 1 to 99% by weight of monoalkyl or monoalkenyl phosphate surfactant having the structure (1):

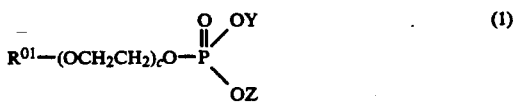

(b) from 1 to 50% by weight of dialkyl or dialkenyl phosphate surfactant having the structure (2):

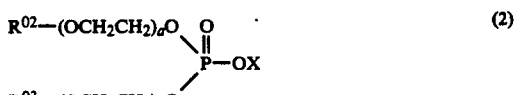

where
$R^{01}$ is chosen from branched or unbranched alkyl and alkenyl groups having an average of from 10 to 18 carbon atoms;
where
$R^{02}$ and $R^{03}$ are each chosen from branched or unbranched alkyl and alkenyl groups having an average of from 10 to 18 carbon atoms;
X, Y and Z are each chosen from H, alkali metal, ammonium and substituted ammonium counterions;
a and b are each chosen from 0 or a value of from 1 to 10, notably 1 to 4, especially 1 or 2; and
c is chosen from 0 or a value of from 1 to 4, especially 1 or 2; and (c) from 1 to 50% by weight of a co-surfactant chosen from:
i. alkylamidopropyl betaines, having the structure (11):

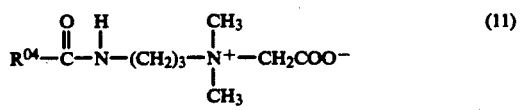

and
ii. alkylamphoglycinates, having the structure (12):

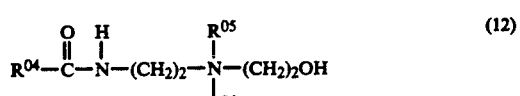

where
$R^{04}$ is $C_{10-16}$ alkyl $R^{05}$ and $R^{06}$ are the same or different and are chosen from $CH_2COO^-$ and $(CH_2)_2COO^-$.

DISCLOSURE OF THE INVENTION

The Monoalkyl or Monoalkenyl Phosphate Surfactant

The composition according to the invention comprises monoalkyl or monoalkenyl phosphate surfactant having the structure (1):

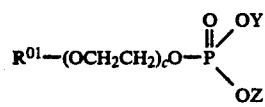

where
$R^{01}$ is chosen from branched or unbranched alkyl and alkenyl groups having from 10 to 18 carbon atoms;
Y and Z are each chosen from H, alkali metal, ammonium and substituted ammonium counterions; and
c is chosen from 0 or a value of from 1 to 4.

Examples of the monoalkyl and monoalkenyl phosphate moiety include:
mono-n-decyl phosphate
mono-n-dodecyl phosphate=(mono-lauryl phosphate)
mono-n-tetradecyl phosphate=(monomyristyl phosphate)
mono-n-hexadecyl phosphate
mono-n-octadecyl phosphate
mono-(diethyleneglycol-mono-n-dodecyl ether) phosphate
mono-(ethyleneglycol-mono-n-decyl ether) phosphate
mono-n-tetradecenyl phosphate
mono-n-hexadecenyl phosphate
mono-n-octadecenyl phosphate
mono-n-decenyl phosphate
mono-n-dodecenyl phosphate
mono-(triethyleneglycol-mono-n-dodecenyl ether) phosphate
mono-(ethyleneglycol-mono-n-tetradecenyl ether) phosphate
mono-7-methyldecyl phosphate
mono-5-methyldodecenyl phosphate
mono-6,6-dimethyltetradecyl phosphate
mono-(ethyleneglycol-mono-n-octadecyl ether) phosphate
mono-(diethyleneglycol-mono-n-octadecenyl ether) phosphate
mono-(polyethyleneglycol[5EO]-monooleyl ether) phosphate
mono-(polyethyleneglycol[3EO]-monolauryl ether) phosphate The monoalkyl phosphate surfactant is preferably a monolauryl phosphate salt.

The amount of the monoalkyl or monoalkenyl phosphate surfactant which is present in the composition according to the invention is from 1 to 99%, preferably from 2 to 50% by weight of the composition, yet more preferably from 10% to 40% by weight of the composition.

The Dialkyl or Dialkenyl Phosphate Surfactant

The composition according to the invention also comprises dialkyl or dialkenyl phosphate surfactant having the structure (2):

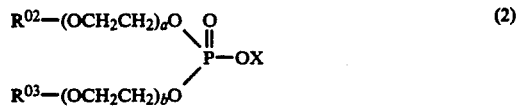

where $R^{02}$ and $R^{03}$ are each chosen from branched or unbranched alkyl and alkenyl groups having an average of from 10 to 18 carbon atoms;
X is chosen from H, alkali metal, ammonium and substituted ammonium counterions; and
a and b are each chosen from 0 or a value of from 1 to 10.

Examples of the dialkyl and dialkenyl phosphate moiety include:
di-n-decyl phosphate
di-n-dodecyl phosphate (dilauryl phosphate)
di-n-tetradecyl phosphate (dimyristyl phosphate)
di-n-hexadecyl phosphate
di-n-octadecyl phosphate
di-n-dodecenyl phosphate
di-(7-methyldecyl) phosphate
di-(ethyleneglycol-mono-n-octadecyl ether) phosphate
di-(diethyleneglycol-mono-n-octadecenyl ether) phosphate
di-(polyethyleneglycol[5EO]-monooleyl ether) phosphate
di-(polyethyleneglycol[3EO]-monolauryl ether) phosphate The preferred dialkyl phosphate salt, is triethanolammonium dilauryl phosphate.

The amount of the dialkyl or dialkenyl phosphate salt which is present in the composition according to the invention is from 1 to 50%, preferably from 1 to 20% or even 10% by weight, of the composition.

The weight ratio of the monoalkyl or monoalkenyl phosphate salt to the dialkyl or dialkenyl phosphate surfactant is from 95:5 to 25:75, preferably 85:15 or 75:25 to 50:50. The total weight of the two surfactants may be 2 to 50% of the composition.

The Co-surfactant

The composition according to the invention also comprises a co-surfactant chosen from:

i. alkylamidopropyl betaines, having the structure (11):

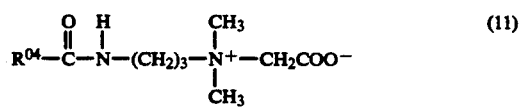

and ii. alkylamphoglycinates, and having the structure (12):

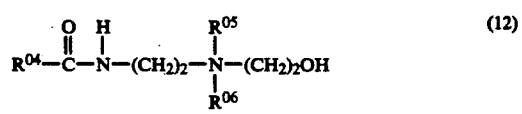

where
$R^{04}$ is $C_{10-16}$ alkyl $R^{05}$ and $R^{06}$ are the same or different and are chosen from $CH_2COO^-$ and $(CH_2)_2COO^-$.

An example of the alkamidopropyl betaine having the structure (11) is:

cocoamidopropyl betaine (e.g. TEGOBETAIN L7, ex Goldschmidt).

Examples of the alkylamphoglycinate having the structure (12) are:

cocoamphodiacetate (e.g. MIRANOL C2M-NP, ex Miranol Inc.)

cocoamphodipropionate (e.g. MIRANOL C2M SF, ex Miranol Inc.)

The amount of co-surfactant which is present in the composition according to the invention is from 1 to 50%, preferably from 2% or even 5% to 40% by weight of the composition.

Water

The composition according to the invention also comprises an amount of water to act as a vehicle for the mono- and di-alkyl or -alkenyl phosphate surfactants and to enable them to be provided at a concentration suitable for convenient topical application to human skin.

The amount of water present in the composition of the invention is accordingly up to 99%, preferably from 5 to 99% by weight of the composition.

Supplementary Surfactant

The composition according to the invention can also optionally comprise a supplementary surfactant, further to modify the surfactant properties attributable to the mono- and di-alkyl or -alkenyl phosphate salts.

Examples of supplementary surfactants include anionic surfactants other than the phosphate salts defined herein, as well as nonionic, amphoteric and zwitterionic surfactants.

Anionic supplementary surfactants

Particularly preferred supplementary surfactants, when employed, are anionic surfactants, examples of which are set out hereinafter.

i Fatty acid soap supplementary surfactant

The composition according to the invention can optionally comprise, as a supplementary surfactant one or more soaps which are water-soluble or water-dispersable alkali metal salts of an organic acid, especially a sodium or a potassium salt, or the corresponding ammonium or substituted ammonium salt. Examples of suitable organic acids are natural or synthetic alkanoic acids having from 10 to 22 carbon atoms, especially the fatty acids of triglyceride oils such as tallow and coconut oil.

For solid products, such as powders, bars or tablets, the preferred soap is a soap of tallow fatty acids, that is fatty acids derived from tallow class fats, for example beef tallow, mutton tallow, lard, palm oil and some vegetable butters. Minor amounts of up to about 30%, preferably 10 to 20%, by weight of sodium soaps of nut oil fatty acids derived from nut oils, for example coconut oil and palm kernel oil, may be admixed with the sodium tallow soaps, to improve their lathering and solubility characteristics if desired. Whereas tallow fatty acids are predominantely $C_{14}$ and $C_{18}$ fatty acids, the nut oil fatty acids are of shorter chain length and are predominantly $C_{10}$–$C_{14}$ fatty acids.

For liquid or gel products, the preferred soaps are predominantely $C_{10-14}$ fatty acids derived from nut oils, or alternatively, from synthetic alkanoic acids.

The soaps can be provided as a preformed ingredient for the composition, or they can be formed in situ during the manufacture of the composition by reaction of suitable fatty acids and an alkali.

The amount of fatty acid soap which can be present in the composition according to the invention is up to 90%, preferably from 2 to 80% by weight of the composition, yet more preferably from 2 to 20% by weight.

ii. Non-soap anionic supplementary surfactants

The composition according to the invention can also optionally comprise one or more non-soap anionic supplementary surfactants, examples of which include:

The alkali metal salts of organic sulphuric reaction products having an alkyl or acyl radical containing from 8-22 carbon atoms and a sulphonic acid or sulphuric acid ester group. Specific examples of these synthetic anionic surfactants are the sodium, ammonium, potassium or triethanolammonium alkyl sulphates, especially those obtained by sulphating the higher alcohols ($C_8$–$C_{18}$), sodium coconut oil fatty acid monoglyceride sulphates and sulphonates; sodium or potassium salts of sulphuric esters of the reaction product of one mole of a higher fatty alcohol (e.g. tallow or coconut oil alcohols) and 1-12 moles of ethyleneoxide; sodium or potassium salts of alkyl phenol ethylene oxide ether sulphate with 1-10 units of ethylene oxide per molecule and in which the alkyl group contains from 8 to 12 carbon atoms, sodium alkyl glyceryl ether sulphonates, the reaction product of fatty acids having from 10 to 22 carbon atoms esterified with isethionic acid and neutralised with sodium hydroxide; water soluble salts of condensation products of fatty acids with N-methyl taurine.

Especially preferred non-soap anionic co-surfactants include:

alkylaryl sulphonates, such as sodium alkyl benzene sulphonate (e.g. TEEPOL CM44, available from Shell).

alkyl sulphates, such as sodium lauryl sulphate (e.g. EMPICOL CX, available from Albright & Wilson), and triethanolomine lauryl sulphate (e.g. EMPICOL TL40/T, available from Albright & Wilson).

alkylether sulphates, such as sodium lauryl ether sulphate (e.g. EMPICOL ESB70, available from Albright & Wilson).

alkyl sulphonates, such as sodium alkane (C13-18) sulphonate (e.g. HOSTAPUR SAS 30, available from Hoechst).

olefin sulphonates, such as sodium olefin sulphonate (C15-18) (e.g. HOSTAPUR OS, available from Hoechst).

Sarcosinates, having the structure (3):

where $R^3$ is chosen from $C_{6-14}$ alkyl, and

M is a counterion chosen from alkali metals, ammonium, substituted ammonium, such as alkanolammonium.

An example of sarcosinates having the structure (3), sodium lauryl sarcosinate (e.g. HAMPOSYL L-95, available from Grace).

Taurides, having the structure (4):

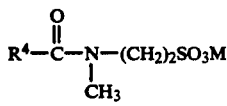

where
R⁴ is chosen from $C_{8-18}$ alkyl

An example of taurides having the structure (4) is: coconut methyl taurine (e.g. FENOPON TC 42, available from GAF).

Isethionates, having the structure (5):

where
R⁵ is chosen from $C_{8-18}$ alkyl.

An example of isethionates having the structure (5) is: sodium acyl isethionate (e.g. JORDAPON C1, available from Jordan).

Monoalkyl sulphosuccinates, having the structure (6):

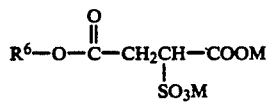

where R⁶ is chosen from $C_{10-20}$ alkyl.

Examples of monoalkyl sulphosuccinates having this structure (6) include:
sodium lauryl sulphosuccinate (e.g. EMPICOL SLL, available from Albright & Wilson)
magnesium alkyl sulphosuccinate (e.g. ELFANOL 616 Mg, available from AKZO),
sodium lauryl ethoxysulphosuccinate (e.g. EMPICOL SDD, available from Albright & Wilson)
coconut monoethanolamide ethoxysulphosuccinate, (e.g. EMPICOL SGG)
disodium lauryl polyglycolether sulphosuccinate (e.g. SURTAGENE S30, available from CHEM-Y)
polyethyleneglycol sulphosuccinate (e.g. REWOPOL SBFA 30, available from REWO).

Dialkyl sulphosuccinates, having the structure (7):

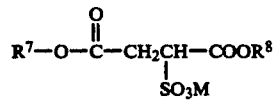

where
R⁷ and R⁸ are the same or different, and are are chosen from $C_{6-14}$ alkyl.

An example of dialkyl sulphosuccinate having the structure (7) is:
sodium dioctyl sulphosuccinate (e.g. EMCOL 4500 available from Witco).

Acyl lactylates, having the structure (8):

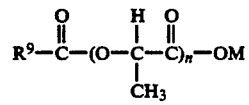

where

R⁹ is chosen from $C_{6-16}$ alkyl.

An example of acyl lactates having the structure (8) is:
decanoyl lactate (e.g. PATIONIC 122A, available from Patterson, C. J.).

Acylated -amino acids, such as sodium lauroyl glutamate (e.g. ACYLGLUTAMATE LS-11, available from Ajinomoto Co. Inc.).

Ethyl carboxylates, such as alkyl $C_{12-14}O(EO)_4OCH_2CO_2Na$ (e.g. AKYPO RLM 38, available from AKZO).

Nonionic supplementary surfactants

A composition according to the invention can also comprise nonionic supplementary surfactants which are compounds produced by the condensation of alkylene oxide groups (hydrophilic in nature) with an organic hydrophobic compound, which may be aliphatic or alkyl aromatic in nature. Examples of nonionic supplementary surfactants include:

i. The polyethylene oxide condensates of alkyl phenols having from 6 to 12 carbon atoms, either straight or branched chain, with ethylene oxide, which is present in amounts of from 10 to 60 moles of ethylene oxide per mole of alkylphenol.

ii. The condensation product of aliphatic alcohols having from 8 to 18 carbon atoms, straight or branched chain, with ethyleneoxide, for example, a coconut alcohol ethyleneoxide condensate having from 10 to 13 moles of ethylene oxide per mole of coconut alcohol, the coconut alcohol fraction having from 10 to 14 carbon atoms.

iii. Long chain tertiary amineoxides having the structure (9):

$$R^{10}R^{11}R^{12}N \rightarrow O \qquad (9)$$

where R¹⁰ contains an alkyl, alkenyl or monohydroxyalkyl radical of from 8 to 18 carbon atoms, from 0 to 10 ethylene oxide moieties and from 0 to 1 glyceryl moiety, and R¹¹ and R¹² contain from 1 to 3 carbon atoms and up to 1 hydroxy group, for example, methyl, ethyl, propyl, hydroxyethyl, or hydroxypropyl groups.

Especially preferred examples of nonionic supplementary surfactants include:
alkylethoxylates, such as the DOBANOL series, available from Shell;
esterethoxylates, such as the TAGAT series, available from Goldschmidt;
alkylalkanolamides, such as coconut monoethanolamide (e.g. EMPILAN CME, available from Albright & Wilson), and coconut diethanolomide, (e.g. EMPILAN CDE, available from Albright & Wilson).
sugar esters, such as sucrose laurate and methyl glucose laurate (available from Grillo-Werke A.G.)
esters of glycols such as ethylene glycol mono stearate.
esters of glycerol, such as glyceryl mono stearate.
ethoxylated sorbitan esters, such as the TWEEN series (available from ICI).
amine oxides, such as alkyldimethyl amine oxide (e.g. EMPIGEN OB, available from Albright & Wilson) and alkylethoxydimethyl amine oxide (e.g. EMPIGEN OY, available from Albright & Wilson).

Zwitterionic and Amphoteric supplementary surfactants

The composition according to the invention can also contain zwitterionic supplementary surfactants, which are derivatives of aliphatic quaternary ammonium, phosphonium and sulphonium compounds in which the aliphatic radicals can be straight or branched chain, and where one aliphatic substituent contains from 8 to 18 carbon atoms, and one contains an anionic water-solubilising group, such as carboxyl, sulphonate, sulphate, phosphate or phosphonate.

Examples of zwitterionic supplementary surfactant include:
4-[N,N-di(2-hydroxyethyl)-N-octadecylammonio]-butane-1-carboxylate, and
5-N,N-di(3-hydroxypropyl)-N-hexadecylammonio]-2-hydroxypentane-1-sulphate.

Particularly preferred zwitterionic supplementary surfactants are betaines, preferred examples of which are:

Alkyl betaines, having the structure (10):

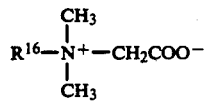

where
$R^{16}$ is $C_{10-16}$ alkyl.

An example of alkyl betaines having the structure (10) is:
lauryldimethyl betaine (e.g. EMPIGEN BB, available from Albright & Wilson).

Sultaines, having the structure (13):

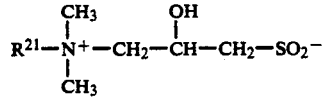

where
$R^{21}$ is chosen from $C_{12-16}$ alkyl or alkylamido.

An example of sultaines having the structure (13) is:
cocoamidopropylhydroxysultaine (e.g. CYCLOTERIC BET-CS, available from Alcolac).

The amount of supplementary surfactant when present in the compositions according to the invention is usually up to 50%, preferably from 1 to 40% by weight.

It is envisaged that the amount of non-soap supplementary surfactant will generally not exceed the amount of the specified co-surfactant.

Optional thickening agent

The composition according to the invention can also comprise a polymer thickener in an amount sufficient to adjust the viscosity of the composition, so as to facilitate dispensing it conveniently onto the body surface.

Examples of polymer thickeners include:
anionic cellulose materials, such as sodium carboxy methyl cellulose;
anionic polymers such as carboxy vinyl polymers, for examples Carbomer 940 and 941;
nonionic cellulose materials, such a methyl cellulose and hydroxy propyl methyl cellulose;
cationic cellulose materials, such as Polymer JR 400;
cationic gum materials, such as Jaguar $C_{13}S$; other gum materials such as gum acacia, gum tragacanth, locust bean gum, guar gum and carrageenan; proteins, such as albumin and protein hydrolysates; and
clay materials, such as bentonite, hectorite, magnesium aluminium silicate, sodium magnesium silicate and a synthetic complex clay having the generic formula:
$[Si_8Mg_{5.1}Li_{0.6}H_{4.6}O_{24}]^{0.6-}$ $Na_{+0.6}$, an example of which is Laponite, available from Laporte Industries.

The amount of thickening agent which can optionally be employed in the composition according to the invention is normally from 0.05 to 5%, preferably 0.1 to 1% by weight of the composition.

Preservative

The composition according to the invention can also optionally comprise a preservative to prevent microbial spoilage, especially biodegradation of the alkyl phosphate salt. It is accordingly apparent that the composition containing the alkyl phosphate salt may be prone to attack by bacteria, moulds and fungi and other microbial influences. There is therefore a risk that the shelf-life of the composition might be unacceptably short due to the biodegradation or spoilage, unless there is included in the composition a bactericide, fungicide or other microbicide in an amount sufficient to inhibit or prevent the said biodegradation or spoilage, or unless other steps are taken to preserve the composition. Examples of preservatives include:

(i) Chemical preservatives, such as ethanol, benzoic acid, sodium benzoate, sorbic acid, potassium sorbate, sodium propionate and the methyl, ethyl, propyl and butyl esters of p-hydroxybenzoic acid 2-bromo-2-nitropropane-1,3-diol, phenoxyethanol, dibromodicyanobutane, formalin and Triclosan. The amount of chemical preservative optionally to be incorporated in the composition according to the invention will generally be from 0.05 to 5%, preferably from 0.1 to 2% by weight, the amount chosen being sufficient to arrest microbial proliferation.

(ii) Water activity depressants, such as glycerol, propylene glycol, sorbitol, sugars and salts, for examples alkali metal halides, sulphates and carboxylates. When employing a water activity depressant, sufficient should be incorporated in the composition according to the invention to reduce the water activity $(a_w)$ from 1 to $<0.9$, preferably to $<0.85$ and most preferably $<0.8$, the lowest of these values being that at which yeasts, moulds and fungi will not proliferate.

Further optional ingredients

The composition according to the invention can also contain other optional adjuncts, that is ingredients other than the main ingredients already defined which are conventionally employed in compositions for topical application to human skin. These adjuncts, when present, will normally form the balance of the composition.

Examples of optional adjuncts include vehicles, the selection of which will depend on the required product form of the composition. Typically, the vehicle when present, will be chosen from diluents, dispersants or carriers for the dialkyl or dialkenyl phosphate salt so as to ensure an even distribution of it when applied to the skin.

Compositions according to this invention can include water as a vehicle, usually with at least one other cosmetically-acceptable vehicle.

Vehicles other than water that can be used in compositions according to the invention can include liquids or solids as emollients, solvents, humectants, thickeners and powders. Examples of each of these types of vehicles, which can be used singly or as mixtures of one or more vehicles, are as follows:

Emollients, such as stearyl alcohol, glyceryl monolaurate, glyceryl monoricinoleate, glyceryl monostearate, propane-1,2-diol, butane-1,3-diol, docosan-1,2-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, tallow, lard, olive oil, palm kernel oil, rapeseed oil, safflower seed oil, soybean oil, sunflower seed oil, olive oil, sesame seed oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate;

Propellants, such as trichlorofluoromethane, dichlorodifluoromethane, dichlorotetrafluoroethane, monochlorodifluoromethane, trichlorotrifluoroethane, propane, butane, isobutane, dimethyl ether, carbon dioxide, nitrous oxide;

Solvents, such as ethyl alcohol, methylene chloride, isopropanol, acetone, castor oil, ethylene glycol monoethyl ether, diethylene glycol monobutyl ether, diethylene glycol monoethyl ether, dimethyl sulphoxide, dimethyl formamide, tetrahydrofuran;

Humectants, such as glycerin, sorbitol, sodium 2-pyrrolidone-5-carboxylate, soluble collagen, dibutyl phthalate, gelatin;

Powders, such as chalk, talc, fullers earth, kaolin, starch, gums, colloidal silicon dioxide, sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The cosmetically acceptable vehicle, when present, will usually form from 0.01 to 99.9%, preferably from 50 to 98% by weight of the composition, and can, in the absence of other cosmetic adjuncts, form the balance of the composition.

PRODUCT FORM OF THE COMPOSITION

The composition according to the invention can take the form of a liquid or gel, intended to be dispensed from a capped Container such as a bottle, roll-on applicator or tube, or a pump-operated or propellant driven aerosol dispenser, as a skin cleanser, shower product, bath additive or shampoo. The composition can also take for form of a powder or a solid such as a stick, preferably housed in a suitable capped holder with a wind-up or push-up action similar to a lip stick, or a bar or tablet, with or without fatty acid soaps, intended to be used for washing instead of a conventional soap bar.

The invention also provides a closed container containing a detergent composition as herein defined.

Process for Preparing the Composition

The invention also provides a process for preparing the composition of the type defined herein, which process comprises the steps of:

(i) preparing a mixture comprising one or more dialkyl and/or dialkenyl phosphate surfactants, as defined herein, and one or more monoalkyl and/or monoalkenyl phosphate surfactants, as defined herein, and one or more co-surfactants, as defined herein; and (ii) subsequently packaging the mixture into containers.

Use of the composition

The composition according to the invention is intended primarily as a personal washing product for cleansing the face and other sensitive parts of the body surface, including the mucosae. It can also be used for washing the hair as well as the skin.

In use, a small quantity, for example from 1 to 5 ml, of the composition is either rubbed between the hands, together with water to form a foam, which is then used for washing, or applied via a flannel or sponge to the area to be cleansed, or the foam is generated directly on that area. The foam is subsequently rinsed away with clean water.

EXAMPLES

The invention is further illustrated by reference to the following examples.

EXAMPLE 1

The foaming of three lauryl phosphate mixtures was investigated. Foaming was measured in vitro by the Ross-Miles procedure. A 0.3% by weight concentration of the alkyl phosphate mixture in water was used, at 20° C. and pH 7.5. Foam is generated by a standard method and the volume of foam is measured as a height in a cylinder.

Foaming was also measured by a trained panel who formed a lather in a standard procedure representing use of the mixture, diluted to 4.5% by weight alkyl phosphate(s), as a product for cleaning the skin. Each panellist estimated the volume and creaminess of the lather as scores on a scale. The lather was also collected and its volume measured.

Results are set out in the following Table 1. The values for estimated/perceived volume and creaminess are totals of panel scores.

TABLE 1

| FOAM PROPERTIES OF MAP:DAP RATIOS | | | | |
|---|---|---|---|---|
| | In vitro | In vivo | | |
| Ratio of MAP:DAP alkyl = lauryl | Foam Height (mm) | Measured Volume (ml) | Estimated/ Volume | Perceived Creaminess |
| 100:0 | 153 | 30 | 118 | 124 |
| 75:25 | 135 | 28 | 96 | 99 |
| 60:40 | 92 | 23 | 52 | 60 |

It is apparent that the presence of dialkyl phosphate inhibits foaming.

EXAMPLE 2

A mixture of monolauryl phosphate and dilauryl phosphate in 75:25 weight ratio was mixed with each of a range of surfactants. The foaming of the resulting mixtures was tested by the Ross-Miles method as in Example 1.

Each test solution contained 0.30% of the alkyl phosphate mixture and 0.06% of the other surfactant(s).

The surfactants used and the foam heights are set out in the following Table 2.

These results show that cocoamidopropyl betaine (CAPB) gave superior foaming and more than overcame the antifoam effect of the dilauryl phosphate.

TABLE 2

LATHER BOOSTING BY CO-ACTIVES

| Co-active | Trade Name | Manufacturer | Foam Height (mm) |
|---|---|---|---|
| CAPB | Tegobetaine L7 | Goldschmidt | 154 |
| Lauryl Sulphoacetate | Nikkol LSA | Nikko Chemicals | 52 |
| Disodium Lauryl Ethoxy Sulphosuccinate | Rewopol SBFA | Rewo | 136 |
| Secondary n-Alkyl Sulphonate | Hostapur SAS | Hoechst | 132 |
| Sodium $\underline{N}$-Cocyl-$\underline{N}$ Methyl Taurate | Fenopon TC42 | Rhone-Poulenc | 136 |
| C9–C11 (6EO) Alcohol Ethoxylate | Dobanol 91-6 | Shell | 129 |
| Sodium Lauryl Ether (2EO) Sulphate | Empicol ESB 70 | Albright & Wilson | 141 |
| Coconut Di Ethanolamide/Coconut Fatty Acid | Cyclomide CD | Witco | 99 |
| Sodium Alkyl PEG-10 Acetate | Marlinat CM105 | Huls | 136 |
| Sodium Isostearyl Lactylate | Crolactil 515L | Croda | 121 |
| Saponin Glycoside | Agrofoam 50 | Paroxite | 141 |
| TEA Lauryl Sulphate | Empicol TL40/% | Albright & Wilson | 106 |
| Coconut Mono Ethanolamide | Empilan CME | Albright & Wilson | 28 |
| Lauryl/Myristyl Dimethyl Amine Oxide | Empigen OB | Albright & Wilson | 18 |

EXAMPLE 3

Mixtures of monolauryl phosphate and dilauryl phosphate were mixed with cocoamidopropyl betaine (CAPB) and diluted to an aqueous solution containing 4.5% by weight alkyl phosphates and 0.8% by weight CAPB. These solutions were assessed by a trained panel as in Example 1.

At the same time a commercial product was diluted to the same alkyl phosphate concentration and tested as a comparison. This product contained mono and dialkyl phosphates in a ratio of >80:<20 (i.e. a mixture containing more than 80% MAP).

The results are set out in the following Table 3.

TABLE 3

| MAP:DAP Ratio | Co-active | Measured Volume (ml) | Estimated/Perceived Volume | Creaminess |
|---|---|---|---|---|
| 75:25 | CAPB | 43 | 123 | 109 |
| 60:40 | CAPB | 36 | 118 | 113 |
| Commercial Product | | 25 | 95 | 133 |

EXAMPLE 4

Mixtures of monolauryl phosphate and dilauryl phosphate were mixed with other materials and assessed by a trained panel for ease of lathering, lather volume and a lather creaminess. The commercial product mentioned in Example 3 was also assessed by the panel. In each case the concentration of alkyl phosphates was 4.5% by weight.

The other materials contained in the mixtures were 0.8% by weight of cocoamidopropyl betaine (CAPB, Tegobetaine L7) or 0.8% by weight of cocoamphodipropionate (Miranol C2M-SF) and 0.4% by weight of cationic cellulosic polymer JR400.

The results (total panel scores) are set out in the following Table 4.

TABLE 4

| System | Ease of Foaming | Volume | Creaminess |
|---|---|---|---|
| MAP:DAP (75:25) | 108.4 | 98.2 | 81.9 |
| MAP:DAP (75:25) + CAPB | 141.2 | 107.1 | 96.9 |
| MAP:DAP (75:25) + CAPB + polymer JR400 | 135.0 | 137.4 | 141.2 |
| MAP:DAP (60:40) + Miranol C2M-SF + polymer JR400 | 133.0 | 129.9 | 130.6 |
| Commercial product | 130.0 | 130.0 | 140.0 |

The mixtures containing CAPB, with and without polymer JR400, were tested for zein solubilisation. This test, first described by Gotte in Proc. Int. Congr. Surface Active Subs. 4th, Brussels, 3 83-90, 1964, tests the liberation of zein (protein from corn kernel) on exposure to surfactant. The result is expressed as percentage nitrogen in supernatant solution and correlates with harshness towards skin.

The results were:

| | |
|---|---|
| MAP:DAP (75:25) + CAPB | 0.68% N |
| above plus 0.4% polymer JR400 | 0.60% N |

Thus inclusion of polymer enhances mildness.

EXAMPLE 5

This Example illustrates a body cleansing liquid product suitable for use in the shower.

The product contains the following ingredients:

| Ingredients | % w/w |
|---|---|
| triethanolamine di-n-lauryl phosphate | 18 |
| triethanolamine mono-n-lauryl phosphate | 18 |
| cocoamphodiacetate (MIRANOL C2M-NP) | 10 |
| preservative | 2 |
| water to | 100 |

This product can be used for cleansing the whole body surface, including the hair, for example under the shower, a convenient amount of say 5 ml being placed in the palm of the hand prior to distributing over the body surface with added water to create a lather with superior volume and creaminess characteristics.

The properties of the above product (the Test product) were tested against another product from which the cocoamphodiacetate was omitted (the Control product).

In this comparative test, strips of polyurethane foam were impregnated with equal quantities of the product according to the invention or the comparative product free from co-surfactant, each product first being diluted with tap water so that the concentration of alkyl phosphate in each case was 1% by weight.

Each member of a panel of twenty assessors was then asked to produce a foam by manually kneading one strip containing the Test product and the other containing the Control product. Each panelist was then asked to decide which of the two samples gave the greater lather volume and the better lather creaminess. None of the panelists knew which sample was which.

The results of this test showed that the lather volume and lather creaminess of the Test product according to the invention containing triethanolamine di-n-lauryl phosphate, triethanolamine mono-n-lauryl phosphate and the cocoampho diacetate was superior to that containing only the triethanolamine di-n-lauryl phosphate and triethanolamine mono-n-lauryl phosphate, this difference being significantly different at the 95% level.

From this test it was concluded that the product according to the invention, the Test product, was superior to the Control product.

Examples 6 to 11 illustrate body shampoos for use in the shower or when bathing.

EXAMPLE 6

| | % w/w |
|---|---|
| triethanolammonium monolauryl phosphate | 18 |
| triethanolammonium dilauryl phosphate | 6 |
| cocoamphodipropionate (MIRANOL C2M-SF) | 5 |
| triethanolammonium laurate | 1 |
| triethanolammonium myristate | 2 |
| lauryldimethylamine oxide | 2 |
| myristyldiethylamine oxide | 0.5 |
| cationised cellulose | 0.1 |
| propylene glycol | 10 |
| water to | 100 |

EXAMPLE 7

| | % w/w |
|---|---|
| triethanolamine monolauryl phosphate | 21 |
| triethanolamine dilauryl phosphate | 9 |
| cocoamidopropyl betaine (TEGOBETAINE L7) | 8 |
| lauryl dimethylbetaine | 3 |
| ethylene glycol monostearate | 1.5 |
| propylene glycol | 2.5 |
| preservative, perfume, dyes | q.v. |
| water to | 100% |

EXAMPLE 8

| | % w/w |
|---|---|
| sodium mono-(diethyleneglycol-mono-n-dodecyl ether) phosphate | 10 |
| sodium di-(diethyleneglycol-mono-n-dodecyl ether) phosphate | 10 |
| cocoamphodiacetate | 12 |
| Triethanolammonium laurate | 1 |
| triethanolammonium myristate | 2 |
| alkyldialkylamine oxide (EMIGEN OB) 30% active) | 8.3 |
| cationised cellulose | 0.1 |
| propylene glycol | 10 |
| water to | 100 |

EXAMPLE 9

| | % w/w |
|---|---|
| triethanolammonium mono-(ethyleneglycol-mono-n-decyl ether) phosphate | 10 |
| triethanolammonium di-(ethyleneglycol-mono-n-octadecenyl ether) phosphate | 8 |
| cocoamphodipropionate (MIRANOL C2M-SF) | 9 |
| lauryl dimethlybetaine | 3 |
| ethylene glycol monostearate | 1.5 |
| propylene glycol | 2.5 |
| preservative, perfume, dyes | q.v. |

| | % w/w |
|---|---|
| water to | 100% |

EXAMPLE 10

| | % w/w |
|---|---|
| triethanolammonium mono-(ethyleneglycol-mono-n-decyl ether) phosphate | 20 |
| triethanolammonium di-(ethyleneglycol-mono-n-octadecyl ether) phosphate | 3 |
| cocoamidopropyl betaine (TEGOBETAINE L7) | 10 |
| triethanolammonium laurate | 1 |
| triethanolammonium myristate | 2 |
| alkyldialkylamine oxide (EMIGEN OB) 30% active) | 8.3 |
| cationised cellulose | 0.1 |
| propylene glycol | 10 |
| water to | 100 |

EXAMPLE 11

| | % w/w |
|---|---|
| sodium mono-(7-methyldecyl) phosphate | 18 |
| sodium di-(7-methyldecyl) phosphate | 12 |
| cocoamphodiacetate | 15 |
| lauryl dimethylbetaine | 3 |
| ethylene glycol monostearate | 1.5 |
| propylene glycol | 2.5 |
| preservative, perfume, dyes | q.v. |
| water to | 100% |

EXAMPLES 12, 13 & 14

The following three examples illustrate soap-containing products in accordance with the invention.

In each case, the products were made in accordance with standard soap manufacture. The product of Example 8 yielded a flaked product which could not readily be pressed into a bar, as the flakes were not sufficiently cohesive. With the products of Examples 9 and 10, bars were formed following the usual plodding, extrusion and stamping that is conventional in soap bar manufacture.

These soap products had the following formulations:

| | Examples | | |
|---|---|---|---|
| | 12 | 13 | 14 |
| Ingredient | (% by weight) | | |
| Hardened Tallow Soap | 59 | 54 | — |
| 80/20 tallow-coco soap | — | 7 | 66 |
| sodium dilauryl phosphate | 4 | 6 | 2 |
| sodium monolauryl phosphate | 12 | 15 | 17 |
| cocoamidopropyl betaine (TEGOBETAINE L7) | 5 | 8 | 10 |
| water | 20 | 10 | 5 |

We claim:
1. A composition suitable for topical application to the skin or hair, which comprises:
   (a) from 1 to 99% by weight of monoalkyl or monoalkenyl phosphate surfactant having the structure (1):

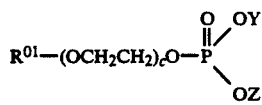

(b) from 1 to 50% by weight of dialkyl or dialkenyl phosphate surfactant having the structure (2):

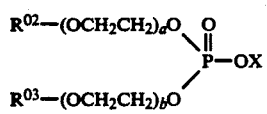

where

R⁰¹ is selected from the group consisting of branched or unbranched alkyl and alkenyl groups having an average of from 10 to 18 carbon atoms;

R⁰² and R⁰³ are each selected from the group consisting of branched or unbranched alkyl and alkenyl groups having an average of from 10 to 18 carbon atoms;

X, Y and Z are each selected from the group consisting of hydrogen, alkali metal, ammonium and substituted ammonium counterions;

a and b are each 0 or a value of from 1 to 10; and c is 0 or a value of from 1 to 4; and (c) from 1 to 50% by weight of a co-surfactant selected from the group consisting of i. alkylamidopropyl betaines, having the structure (11):

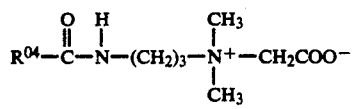

and ii. alkylamphoglycinates, having the structure (12):

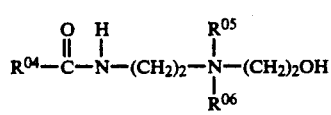

where

R⁰⁴ is C₁₀₋₁₆ alkyl

R⁰⁵ and R⁰⁶ are the same or different and are selected from CH₂COO⁻ and (CH₂)₂COO⁻

(d) a cationic cellulosic polymer present in an effective amount to enhance mildness.

2. A composition according to claim 1, in which the monoalkyl phosphate surfactant is selected from the group consisting of:
mono-n-decyl phosphate
mono-n-dodecyl phosphate=(mono-lauryl phosphate)
mono-n-tetradecyl phosphate=(monomyristyl phosphate)
mono-n-hexadecyl phosphate
mono-n-octadecyl phosphate
mono-(diethyleneglycol-mono-n-dodecyl ether) phosphate
mono-ethyleneglycol-mono-n-decyl ether) phosphate
mono-n-tetradecenyl phosphate
mono-n-hexadecenyl phosphate
mono-n-octadecenyl phosphate
mono-n-decenyl phosphate
mono-n-dodecenyl phosphate
mono-(triethyleneglycol-mono-n-dodecenyl ether) phosphate
mono-(ethyleneglycol-mono-n-tetradecenyl ether) phosphate
mono-7-methyldecyl phosphate
mono-5-methyldodecyl phosphate
mono-6,6-dimethyltetradecyl phosphate
mono-(ethyleneglycol-mono-n-octadecyl ether) phosphate
mono-(diethyleneglycol-mono-n-octadecenyl ether) phosphate
mono-(polyethyleneglycol[5EO]-monooleyl ether) phosphate
mono-(polyethyleneglycol[3EO]-monolauryl ether) phosphate.

3. A composition according to claim 1 in which the monoalkyl phosphate surfactant is mono-n-dodecyl phosphate salt.

4. A composition according to claim 1 in which the monoalkyl or monoalkenyl phosphate surfactant forms from 2 to 50% by weight of the composition.

5. A composition according to claim 1 in which the dialkyl phosphate surfactant is selected from the group consisting of:
di-n-decyl phosphate
di-n-dodecyl phosphate (dilauryl phosphate)
di-n-tetradecyl phosphate (dimyristyl phosphate)
di-n-hexadecyl phosphate
di-n-octadecyl phosphate
di-n-dodecenyl phosphate
di-(7-methyldecyl) phosphate
di-(ethyleneglycol-mono-n-octadecyl ether) phosphate
di-(diethyleneglycol-mono-n-octadecenyl ether) phosphate
di-(polyethyleneglycol[5EO]-monooleyl ether) phosphate
di-(polyethyleneglycol[3EO]-monolauryl ether) phosphate 6. A composition according to claim 1 in which the dialkyl phosphate surfactant is a sodium, a potassium or a triethanolamine salt.

7. A composition according to claim 1 in which the dialkyl phosphate surfactant forms from 1 to 10% by weight of the composition.

8. A composition according to claim 1 in which the weight ratio of the monoalkyl or monoalkenyl phosphate surfactant to the dialkyl or dialkenyl phosphate surfactant is from 95:5 to 25:75.

9. A composition according to claim 1 in which the weight ratio of the monoalkyl or monoalkenyl phosphate surfactant to the dialkyl or dialkenyl phosphate surfactant is from 75:25 to 50:50.

10. A composition according to claim 1 which further comprises a supplementary anionic surfactant.

11. A composition according to claim 1 which further comprises a supplementary nonionic surfactant.

12. A composition according to claim 1 which further comprises a supplementary zwitterionic surfactant.

13. A composition according to claim 1 which is a liquid or gel product.

14. A composition according to claim 13, which further comprises a polymeric thickener.

15. A composition according to claim 1 which is a shampoo.

16. A composition according to claim 1 which is a powder.

17. A composition according to claim 1 which is a bar or tablet suitable for washing the skin.

18. A process for preparing a composition according to claim 1 which process comprises the steps of: i. preparing a mixture comprising:
   a. 1 to 99% by weight of one or more monoalkyl or monoalkenyl phosphate surfactants having the structure (1):

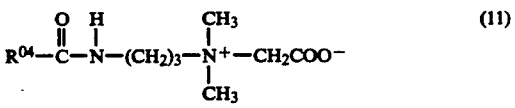

b. 1 to 50% by weight of one or more dialkyl or dialkenyl phosphate surfactants having the structure (2):

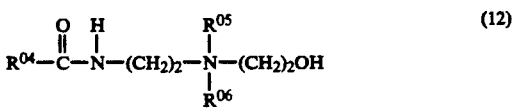

$R^{01}$ is selected from the group consisting of branched or unbranched alkyl and alkenyl groups having an average of from 10 to 18 carbon atoms;
where
   $R^{02}$ and $R^{03}$ are each selected from the group consisting of branched or unbranched alkyl and alkenyl groups having an average of from 10 to 18 carbon atoms;

X, Y and Z are each selected from the group consisting of H, alkali metal, ammonium and substituted ammonium counterions;
a and b are each 0 or a value of from 1 to 10;
c is 0 or a value of from 1 to 4; and c. 1 to 50% by weight of a co-surfactant selected from the group consisting of
      i. alkylamidopropyl betaines, having the structure (11):

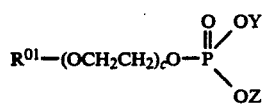

and
      ii. alkylamphoglycinates, having the structure (12):

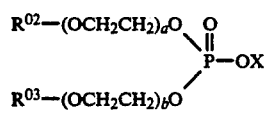

where
   $R^{04}$ is $C_{10-16}$ alkyl
   $R^{05}$ and $R^{06}$ are the same or different and are selected from the group consisting of $CH_2COO^-$ and $(CH_2)_2COO^-$; and d. a cationic cellulosic polymer present in an effective amount to improve mildness;
   ii. subsequently packaging the composition so formed.

19. A method of washing human skin or hair characterised by applying to said skin or hair a composition according to claim 1.

* * * * *